(12) United States Patent
Arita et al.

(10) Patent No.: US 12,121,428 B2
(45) Date of Patent: Oct. 22, 2024

(54) ABSORBENT ARTICLE HAVING ELASTIC MEMBERS

(71) Applicant: KAO CORPORATION, Tokyo (JP)

(72) Inventors: Kosuke Arita, Utsunomiya (JP); Akiyuki Ueda, Utsunomiya (JP); Yuko Fukuda, Mashiko-machi (JP); Yasuyuki Okuda, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1140 days.

(21) Appl. No.: 16/958,345

(22) PCT Filed: Dec. 27, 2017

(86) PCT No.: PCT/JP2017/047070
§ 371 (c)(1),
(2) Date: Jun. 26, 2020

(87) PCT Pub. No.: WO2019/130510
PCT Pub. Date: Jul. 4, 2019

(65) Prior Publication Data
US 2021/0059869 A1    Mar. 4, 2021

(51) Int. Cl.
*A61F 13/494* (2006.01)
*A61F 13/49* (2006.01)

(52) U.S. Cl.
CPC .. *A61F 13/494* (2013.01); *A61F 2013/49092* (2013.01); *A61F 2013/4948* (2013.01)

(58) Field of Classification Search
IPC ........ A61F 13/494,13/475, 13/49, 2013/49028, 13/49017, 2013/49026
See application file for complete search history.

(56) References Cited

U.S. PATENT DOCUMENTS

| 6,156,023 A | 12/2000 | Yoshioka |
| 7,879,017 B1 | 2/2011 | Tabata et al. |

(Continued)

FOREIGN PATENT DOCUMENTS

| CN | 1230395 A | 10/1999 |
| CN | 1615806 A | 5/2005 |

(Continued)

OTHER PUBLICATIONS

Extended European Search Report for European Application No. 17936193.6, dated Jul. 16, 2021.

(Continued)

*Primary Examiner* — Michele Kidwell
(74) *Attorney, Agent, or Firm* — Birch, Stewart, Kolasch & Birch, LLP (57) ABSTRACT

An absorbent article (1) of the present invention includes a leg cuff (24). The leg cuff (24) has leg elastic members (25). The leg cuff (24) can be divided, by an imaginary line (IL) passing through the center (ct) between an outermost leg elastic member (25s) that is located farthest outward and an innermost leg elastic member (25i) that is located farthest inward, into a leg cuff first region (ST) that extends from the imaginary line (IL) up to and including the outermost leg elastic member (25s) and a leg cuff second region (IT) that extends from the imaginary line (IL) up to and including the innermost leg elastic member (25i). When the elongation amount of the leg cuff first region (ST) and the leg cuff second region (IT) in a natural state is defined as 0, and the elongation amount thereof in a maximally stretched state is defined as 100, the stress in the leg cuff first region (ST) is greater than the stress in the leg cuff second region (IT) when the elongation amount is 5. Moreover, the stress in the leg cuff second region (IT) is greater than the stress in the leg cuff first region (ST) when the elongation amount is 100.

17 Claims, 5 Drawing Sheets

(56) References Cited

U.S. PATENT DOCUMENTS

| | | | |
|---|---|---|---|
| 10,792,198 B2 * | 10/2020 | Surushe | A61F 13/4942 |
| 2001/0003153 A1 * | 6/2001 | Sayama | A61F 13/4942 604/385.28 |
| 2001/0025165 A1 | 9/2001 | Shimoe | |
| 2002/0193775 A1 | 12/2002 | Shimoe | |
| 2003/0088226 A1 | 5/2003 | Takagi et al. | |
| 2009/0054862 A1 | 2/2009 | Tatsukawa | |
| 2010/0057036 A1 | 3/2010 | Sperl et al. | |
| 2013/0041340 A1 | 2/2013 | Kawakami et al. | |
| 2014/0163510 A1 | 6/2014 | Sperl et al. | |
| 2015/0366724 A1 * | 12/2015 | Fukuzawa | A61F 13/496 604/385.01 |
| 2020/0289340 A1 * | 9/2020 | Arita | A61F 13/4752 |

FOREIGN PATENT DOCUMENTS

| | | |
|---|---|---|
| CN | 102905665 A | 1/2013 |
| EP | 1 108 409 A2 | 6/2001 |
| EP | 1 219 274 A1 | 7/2002 |
| JP | 2001-25485 A | 1/2001 |
| JP | 2001-269368 A | 10/2001 |
| JP | 2003-135523 A | 5/2003 |
| JP | 2006-223881 A | 8/2006 |
| JP | 2007-75277 A | 3/2007 |
| JP | 2014-42742 A | 3/2014 |
| JP | 2014-171692 A | 9/2014 |
| RU | 2 498 791 C2 | 11/2013 |
| WO | 97/15260 * | 5/1997 ............. A61F 13/15 |

OTHER PUBLICATIONS

International Search Report, issued in PCT/JP2017/047070, PCT/ISA/210, dated Mar. 27, 2018.

* cited by examiner

ABSORBENT ARTICLE HAVING ELASTIC MEMBERS

TECHNICAL FIELD

The present invention relates to an absorbent article provided with leg cuffs.

BACKGROUND ART

In absorbent articles such as disposable diapers and sanitary napkins, in order to improve the fit of such an absorbent article to the circumferences of the legs of a wearer and prevent leakage of a liquid from the absorbent article in a state in which the absorbent article is worn, there are cases in which leg cuffs are provided on the outer side of two lateral side portions of an absorbent member that extend in a longitudinal direction of the absorbent member, and the leg cuffs extend along those lateral side portions. For example, Patent Literature 1 discloses an absorbent article in which elastic side flaps are provided on the outer side of two lateral side portions of an absorbent member, an elastic region of each elastic side flap is provided on a free end portion side thereof, and when the elastic region is divided into a first elastic region that is located on the free end portion side and a second elastic region that is located inward of the first elastic region in a lateral direction, the extension stress in the first elastic region is lower than the extension stress in the second elastic region.

Also, Patent Literature 2 discloses a disposable absorbent article in which stand-up cuffs are provided on the outer side of two lateral side portions of an absorbent member, and each stand-up cuff has, in a state of being stretched in the longitudinal direction, a stand-up portion that extends from a stand-up end of the stand-up cuff toward a central side of the absorbent article and a planar contact portion that is folded back midway so as to be inverted and extends outward. In the disposable absorbent article disclosed in Patent Literature 2, a plurality of elastic stretch members are arranged at intervals in a width direction in each of the planar contact portion and the stand-up portion.

CITATION LIST

Patent Literature

Patent Literature 1: JP 2014-171692A
Patent Literature 2: JP 2001-25485A

SUMMARY OF INVENTION

The present invention provides an absorbent article including a liquid-retentive absorbent member, and a leg cuff extending outward in a width direction from each of two lateral side portions of the absorbent member that extend in a longitudinal direction, the leg cuff extending along the lateral side portion. Two or more leg elastic members extending in the longitudinal direction are arranged in the leg cuff in a stretched state. The leg cuff is divided, by an imaginary line extending in the longitudinal direction through a center in the width direction between, out of the leg elastic members, an outermost leg elastic member located farthest outward in the width direction and an innermost leg elastic member located farthest inward in the width direction, into a leg cuff first region that extends from the imaginary line up to and including the outermost leg elastic member and a leg cuff second region that extends from the imaginary line up to and including the innermost leg elastic member. When an elongation amount of the leg cuff first region and the leg cuff second region in a natural state is defined as 0, and the elongation amount thereof in a maximally stretched state is defined as 100, stress in the leg cuff first region is greater than stress in the leg cuff second region when the elongation amount is 5. Stress in the leg cuff second region is greater than stress in the leg cuff first region when the elongation amount is 100.

DESCRIPTION OF EMBODIMENTS

The fit of an absorbent article to the circumferences of the legs of a wearer tends to be improved by providing the absorbent article with leg cuffs. However, due to movements of the wearer, how firmly the leg cuffs are in contact with the circumferences of the legs of the wearer changes from a wearing state immediately after the absorbent article is put on, resulting in a decrease in the fit of the absorbent article to the circumferences of the legs of the wearer, and a gap that may contribute to the occurrence of liquid leakage may be formed between the absorbent article and the circumferences of the legs of the wearer. If an attempt to realize strong stretching stress in the leg cuffs from the time when the wearer puts on the absorbent article is made in order to prevent the formation of such a gap, a compression mark or the like caused by the leg cuffs will be formed on the circumferences of the legs while the absorbent article is worn, and the burden on the wearer will increase. Patent Literatures 1 and 2 make no mention whatsoever of a leg cuff that is unlikely to form a gap immediately after the absorbent article is put on and during the time the absorbent article is worn and that is also unlikely to form a compression mark due to the leg cuff.

The present invention relates to an improvement of an absorbent article having leg cuffs, and more particularly relates to an absorbent article in which: leg cuffs are prevented from protruding into a crotch portion immediately after the absorbent article is put on and narrowing a hydrophilic width (area in which bodily fluid can be absorbed); the leg cuffs conform to the circumferences of the legs of the wearer without leaving any gap and can thus prevent leakage even in a state in which the distances between the absorbent article and the circumferences of the legs of the wearer change due to movements of the wearer and a crotch space is formed; and the leg cuffs are unlikely to form a compression mark on the circumferences of the legs of the wearer while the absorbent article is worn.

Hereinafter, the present invention will be described based on preferred embodiments thereof with reference to the drawings. FIGS. 1 to 4 show a schematic configuration of a pull-on disposable diaper 1, which is an embodiment of an absorbent article of the present invention. The diaper 1 includes a below-waist portion that is placed below the waist of the wearer when the diaper is worn, and the below-waist portion is divided into a front portion 1A and a rear portion 1C that are placed on an anterior side and a posterior side, respectively, of the wearer when the diaper is worn. The diaper 1 has the front portion 1A and the rear portion 1C, as well as a crotch portion 1B that is located between the front and rear portions. The diaper 1 has a longitudinal direction X that corresponds to an anterior-posterior direction of the wearer and extends from the front portion 1A to the rear portion 1C via the crotch portion 1B, and a width direction Y that is perpendicular to the longitudinal direction X.

Figure 1:
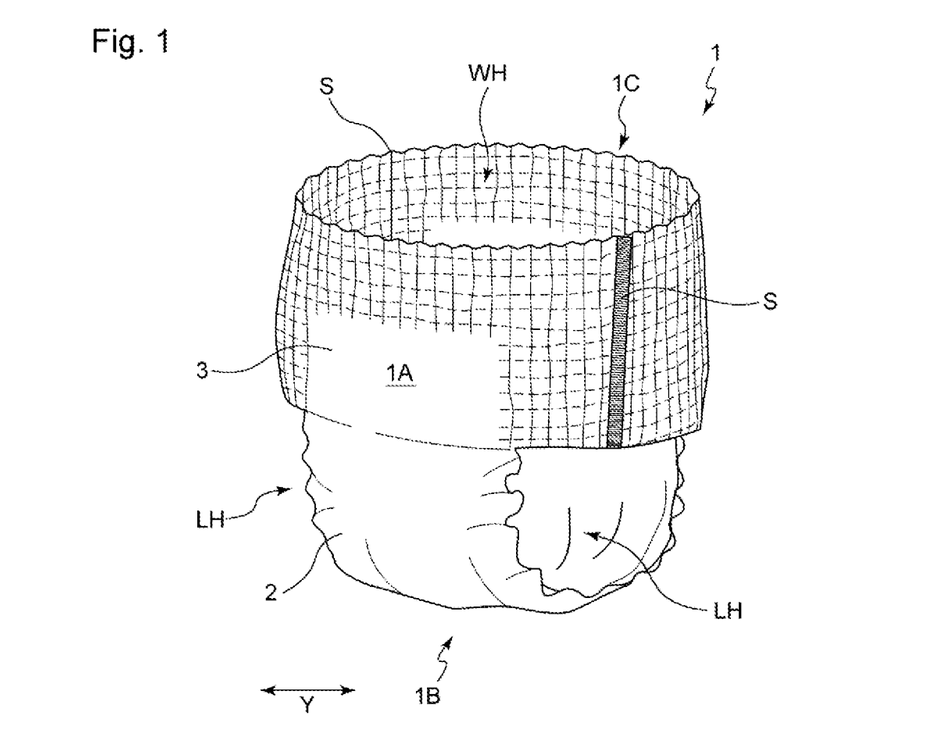
FIG. 1 is a perspective view schematically showing a pull-on disposable diaper, which is an embodiment of an absorbent article of the present invention.
Figure 2:
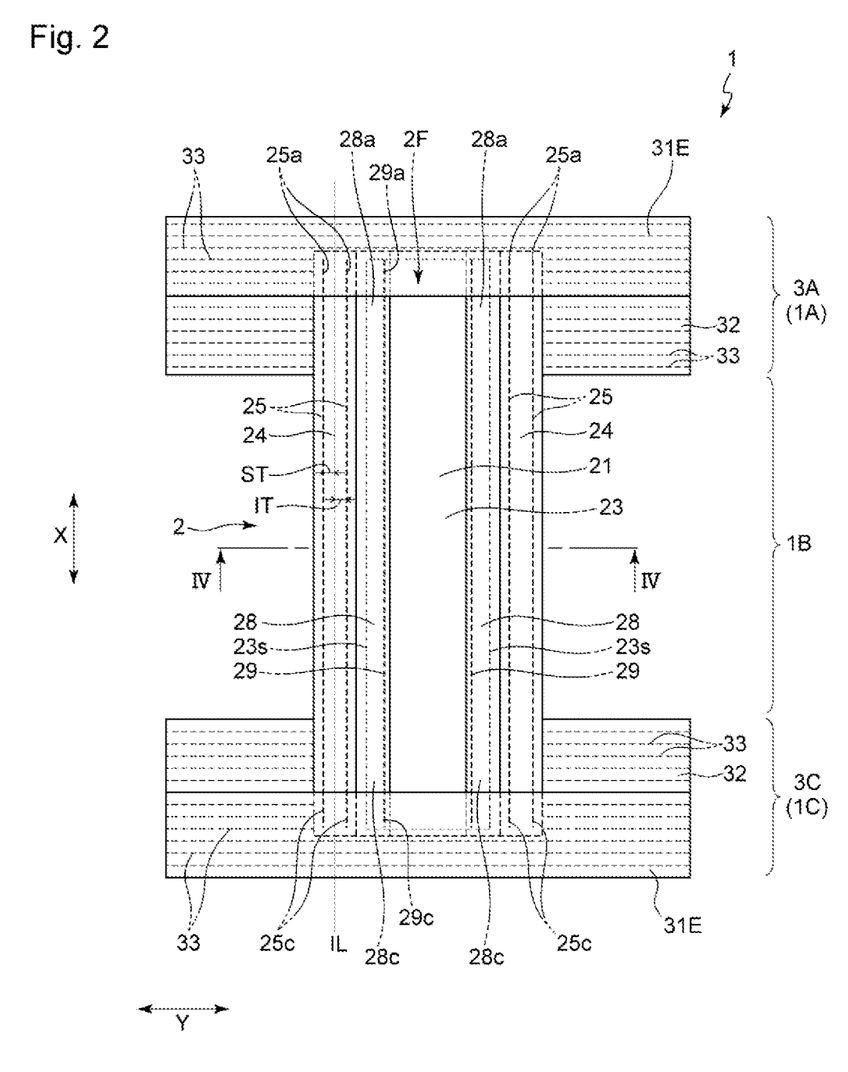
FIG. 2 is a flat-out planar view schematically showing a skin-facing surface side of the diaper shown in FIG. 1 in its flat-out, uncontracted state.
Figure 3:
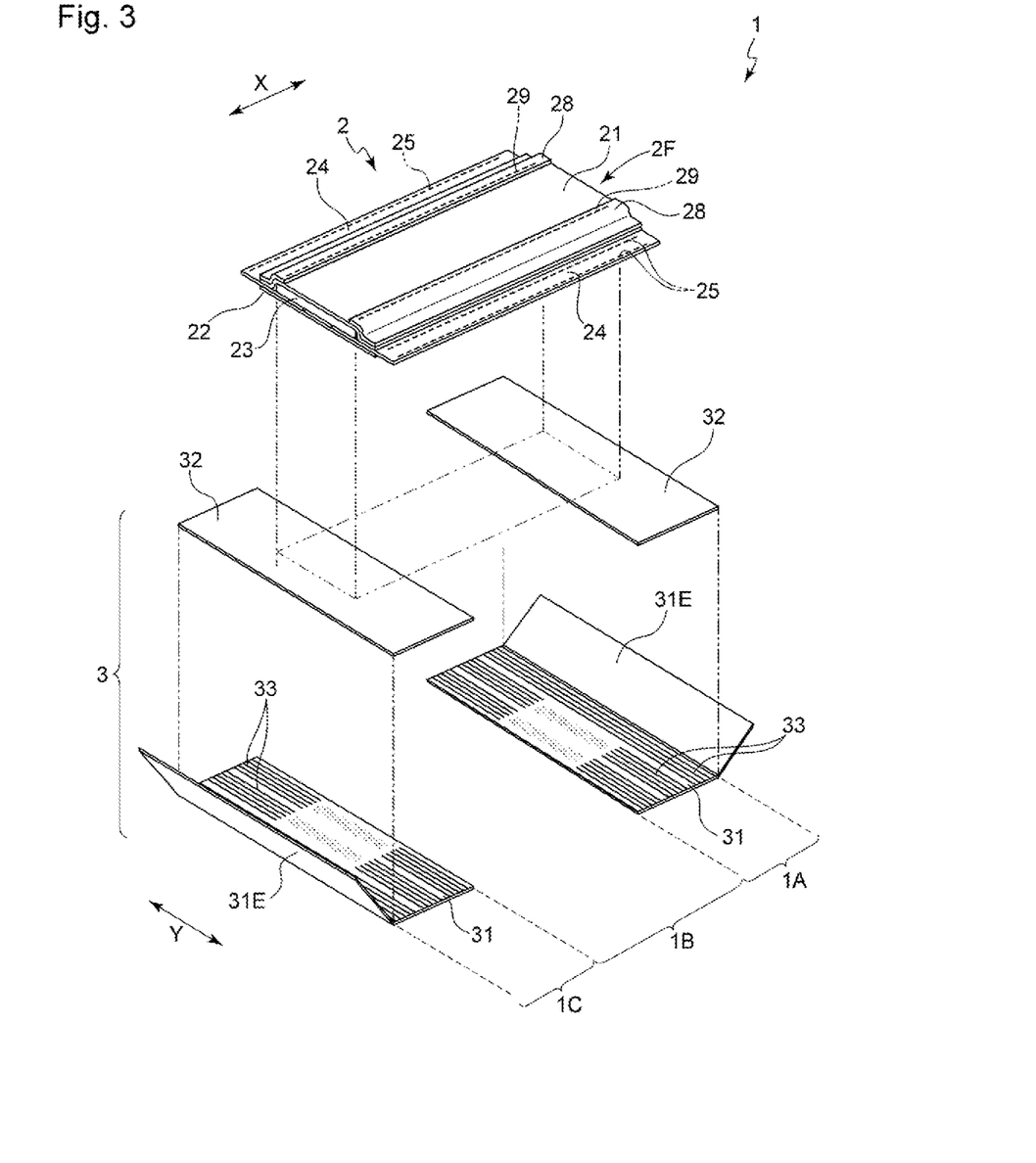
FIG. 3 is an exploded perspective view schematically showing the diaper shown in FIG. 1, in an exploded manner.

As shown in FIGS. 2 and 3, the diaper 1 has an absorbent assembly 2 having a liquid-retentive absorbent member 23 that is oblong in the longitudinal direction X, a topsheet 21 that is arranged on a skin-facing surface of the absorbent member 23, and a backsheet 22 that is arranged on a non-skin-facing surface of the absorbent member 23, as well as an outer cover 3 that is located on a non-skin-facing surface side of the absorbent assembly 2 and to which the absorbent assembly 2 is fixed. In the diaper 1, as shown in FIG. 1, two lateral side portions of the outer cover 3 in the front portion 1A, the lateral side portions extending in the longitudinal direction X, are respectively joined to two lateral side portions of the outer cover 3 in the rear portion 1C, the lateral side portions extending in the longitudinal direction X, and thus, a pair of side seals S and S, a waist opening WH into which the waist of the wearer is to be inserted, and a pair of leg openings LH and LH into which the legs of the wearer are to be inserted are formed.

In this description, "skin-facing surface" refers to a surface of the diaper 1 or a constituent member thereof (e.g., the topsheet 21) that faces the skin of the wearer when the diaper 1 is worn, that is, a side that is relatively close to the skin of the wearer, and "non-skin-facing surface" refers to a surface of the diaper 1 or a constituent member thereof that faces a side that is opposite to the skin of the wearer when the diaper 1 is worn, that is, a side that is relatively far from the skin of the wearer. Note that "when the diaper is worn" as used herein means a state in which an ordinary proper wearing position, that is, a correct wearing position of the disposable diaper 1 is maintained.

The absorbent assembly 2 has an oblong rectangular shape in a planar view as indicated by the contour lines in FIG. 2, and extends from the front portion 1A to the rear portion 1C. The absorbent assembly 2 is fixed to a central portion in the width direction Y of the outer cover 3, with the longitudinal direction of the absorbent assembly 2 matching the longitudinal direction X of the diaper 1 in its flat-out, uncontracted state. As shown in FIG. 2, the outer cover 3 forms the external shape of the diaper 1 when the diaper 1 is in its flat-out, uncontracted state. The "flat-out, uncontracted state" of the diaper 1 means a state in which the side seals S are peeled apart so that the diaper 1 is in a flat-out state, and the diaper 1 in the flat-out state is spread out by stretching elastic members in respective portions of the diaper to such an extent that the dimensions of the diaper match its design dimensions, that is, the dimensions when the diaper 1 is spread out in a planar shape while completely eliminating the influence of the elastic members.

As shown in FIG. 3, the absorbent assembly 2 includes the liquid permeable topsheet 21 that forms the skin-facing surface, the liquid impermeable or sparingly liquid permeable, or water repellent backsheet 22 that forms the non-skin-facing surface, and the liquid-retentive absorbent member 23 that is positioned between the sheets 21 and 22, and these components are integrated into the absorbent assembly 2 with use of a known joining means such as an adhesive. The absorbent member 23 is located in a central portion in the width direction Y of the diaper 1. As the topsheet 21 and the backsheet 22, individually, various types of members conventionally used for absorbent articles of this type can be used without any specific limitation. For example, various types of nonwoven fabrics, apertured films, and the like can be used as the topsheet 21. Resin films, laminates of a resin film and a nonwoven fabric or the like, and the like can be used as the backsheet 22.

As shown in FIG. 3, the absorbent member 23 has a substantially oblong rectangular shape extending in the longitudinal direction X in a planar view, and spans from the front portion 1A to the rear portion 1C. The absorbent member 23 includes a liquid-retentive absorbent core (not shown) containing an absorbent material, and a core-wrap sheet (not shown) that covers the skin-facing surface and the non-skin-facing surface of the absorbent core. The absorbent core and the core-wrap sheet are joined to each other using a known joining means such as a hot-melt adhesive.

The absorbent core is formed by fiber stacking a core forming material that contains the absorbent material. As the absorbent material, materials normally used as a material for forming absorbent cores of this type can be used without any specific limitation. Examples of the material for forming absorbent cores include wood pulp, hydrophilic fibers such as synthetic fibers treated with a hydrophilization agent, and water-absorbent polymer particles. The absorbent core may be constituted by a fiber stack of hydrophilic fibers, or the fiber stack with water-absorbent polymer particles supported thereon. A water permeable sheet material can be used as the core-wrap sheet, and examples thereof include paper, a nonwoven fabric, and the like. The absorbent core may have a monolayered structure or a multilayered structure in accordance with a specific use of the diaper 1.

As shown in FIGS. 2 and 3, the diaper 1 includes, in two lateral side regions of the absorbent assembly 2 that extend in the longitudinal direction X, a pair of leg cuffs 24 and 24 extending outward in the width direction Y from lateral side portions 23s of the absorbent member 23 that extend in the longitudinal direction X. The leg cuffs 24 extend in the longitudinal direction X along the lateral side portions 23s of the absorbent member 23, and span from the front portion 1A to the rear portion 1C. Moreover, the diaper 1 includes, in the two lateral side regions extending in the longitudinal direction X of the absorbent assembly 2, a pair of leak-proof cuffs 28 and 28 that are located inward of the respective leg cuffs 24 and 24 in the width direction Y. The leak-proof cuffs 28 extend in the longitudinal direction X along the lateral side portions 23s of the absorbent member 23, and span from the front portion 1A to the rear portion 1C. The leg cuffs 24 and the leak-proof cuffs 28 are configured such that, due to contraction of elastic members arranged therein in a stretched state, the cuffs stand up in the crotch portion 1B when the diaper 1 is worn, thereby stopping excreted fluid such as urine from flowing out in the width direction Y. Details of the leg cuffs 24 and the leak-proof cuffs 28 will be described later.

As shown in FIGS. 2 and 3, the outer cover 3 has a front outer cover 3A that is located in the front portion 1A and a rear outer cover 3C that is located in the rear portion 1C. The front outer cover 3A and the rear outer cover 3C are placed below the waist of the wearer when the diaper 1 is worn, and have a rectangular shape when the diaper 1 is in its flat-out, uncontracted state. The crotch portion 1B has an excretory-portion-facing portion that is placed so as to face an excretory portion of the wearer when the diaper 1 is worn, and the excretory-portion-facing portion is usually located in or near a central portion in the longitudinal direction X of the diaper 1.

The front outer cover 3A and the rear outer cover 3C have similar configurations. Therefore, in the following description, the configurations of the front outer cover 3A and the rear outer cover 3C will be described using mainly the front outer cover 3A as an example, but a similar description also applies to the rear outer cover 3C as well. Note that, however, the absorbent article of the present invention is not limited to an absorbent article in which the front outer cover 3A and the rear outer cover 3C have similar configurations. Also, it is possible that only one of the front outer cover 3A and the rear outer cover 3C has a folded-back portion 31E that is configured as described later.

As shown in FIGS. 2 and 3, the front outer cover 3A includes an outer sheet 31 that forms the outer surface, that is, the non-skin-facing surface of the diaper 1, an inner sheet 32 that is adjacent to the outer sheet 31 and is located on a skin-facing surface side of the outer sheet 31, and a plurality of below-waist elastic members 33 that are arranged between the sheets 31 and 32. In the front outer cover 3A, which constitutes the front portion 1A, the plurality of below-waist elastic members 33 are arranged at intervals in the longitudinal direction X stretched in the width direction Y. The below-waist elastic members 33 are filamentous or continuous members, and are sandwiched and fixed between the outer sheet 31 and the inner sheet 32 with use of an adhesive. Both the outer sheet 31 and the inner sheet 32 of the diaper 1 are non-elastic sheets that do not have elasticity, but the below-waist elastic members 33 are arranged between the sheets 31 and 32 of the front outer cover 3A stretched in the width direction Y, and since the plurality of below-waist elastic members 33 have elasticity in the width direction Y, the entire front outer cover 3A is elasticized in the width direction Y. Waist gathers are formed in an opening edge portion of the waist opening WH of the front outer cover 3A by some of the below-waist elastic members 33.

In the front outer cover 3A, as shown in FIGS. 2 and 3, the outer sheet 31 extends from an end edge in the longitudinal direction X of the inner sheet 32 and is folded back toward the skin-facing surface of the inner sheet 32, and thus, the outer sheet 31 has a folded-back portion 31E. The folded-back portion 31E covers a front end portion 2F in the longitudinal direction X of the absorbent assembly 2 and is joined to the topsheet 21 of the absorbent assembly 2 and the inner sheet 32. The joining means is not particularly limited, and a known joining means such as an adhesive or fusion-bonding can be used. As the outer sheet 31 and the inner sheet 32, individually, various types of members conventionally used for absorbent articles of this type can be used without any specific limitation, and examples thereof include various types of hydrophobic nonwoven fabrics and the like.

Figure 4:
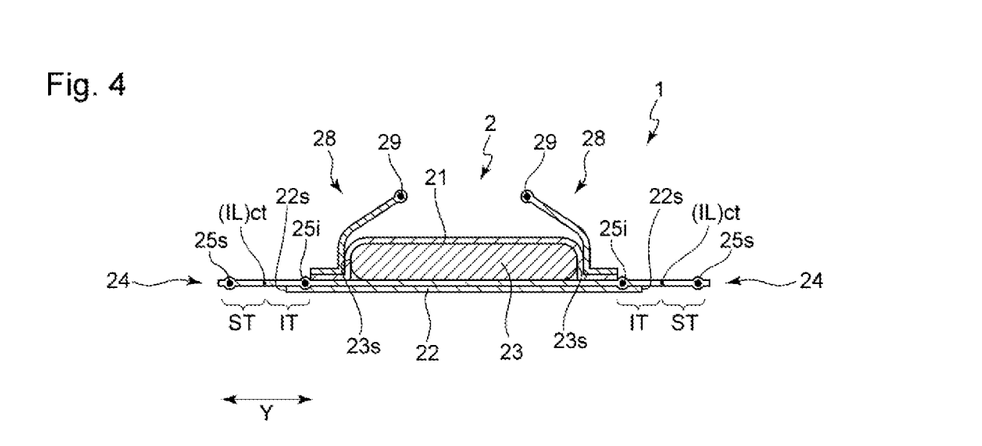
FIG. 4 is a cross-sectional view taken along line IV-IV in FIG. 2.

In the leg cuffs 24, two or more leg elastic members 25 extending in the longitudinal direction X are arranged in a stretched state. In the case of the diaper 1, as shown in FIG. 4, two leg elastic members 25 and 25 are arranged in each of the leg cuffs 24. For example, the leg cuffs 24 are formed by obtaining sheet members in each of which a single sheet for constituting a leg cuff 24 is folded in half, and the leg elastic members 25 in a stretched state are arranged between the two halves of the half-folded sheet and fixed thereto with use of an adhesive or the like, and fixing the obtained sheet members, with use of an adhesive or the like, between the topsheet 21 and the backsheet 22 in the two lateral side regions extending in the longitudinal direction X of the absorbent assembly 2. Note that, instead of folding a single sheet for constituting a leg cuff 24 in half, it is also possible to form a leg cuff 24 by obtaining a sheet member in which the leg elastic members 25 in a stretched state are arranged on one of the two faces of the sheet and fixed thereto using an adhesive or the like, and fixing the obtained sheet member to the non-skin-facing surface of the backsheet 22 of the absorbent assembly 2 with use of an adhesive or the like.

As shown in FIGS. 2 and 4, each leg cuff 24, in a maximally stretched state, can be divided by an imaginary line IL extending in the longitudinal direction X through the center ct in the width direction between an outermost leg elastic member 25$s$ and an innermost leg elastic member 25$i$, out of the two leg elastic members 25 and 25, the outermost leg elastic member 25$s$ being located farthest outward in the width direction Y and the innermost leg elastic member 25$i$ being located farthest inward in the width direction Y, into a leg cuff first region ST that extends from the imaginary line IL up to and including the outermost leg elastic member 25$s$ and a leg cuff second region IT that extends from the imaginary line IL up to and including the innermost leg elastic member 25$i$. The "maximally stretched state" refers to a state in which a leg cuff 24 extending from the front portion 1A to the rear portion 1C is cut off from a lateral side edge of the lateral side portion 23$s$ extending in the longitudinal direction X of the absorbent member 23, and the leg cuff 24 is spread out so that the dimensions thereof match its design dimensions in a state in which the leg elastic members 25 are removed, that is, the dimensions when the leg cuff 24 is spread out in a planar shape while completely eliminating the influence of the leg elastic members 25. In the leg cuff 24 in its maximally stretched state, the imaginary line IL extends in a straight line along the longitudinal direction X. The leg cuff first region ST is a region between the imaginary line IL and an outer edge in the width direction (direction X) of the outermost leg elastic member 25$s$, and includes at least the outermost leg elastic member 25$s$. In the maximally stretched state, the leg cuff first region ST extends in the longitudinal direction X and has a substantially rectangular shape in a planar view. Similarly, the leg cuff second region IT is a region between the imaginary line IL and an inner edge in the width direction (direction X) of the innermost leg elastic member 25$i$, and includes at least the innermost leg elastic member 25$i$. In the maximally stretched state, the leg cuff second region IT extends in the longitudinal direction X and has a substantially rectangular shape in a planar view.

The leg cuff first region ST and the leg cuff second region IT are characterized by a difference in extensibility when these regions are stretched. More specifically, when the elongation amount of the leg cuff first region ST and the leg cuff second region IT in a natural state is defined as 0, and the elongation amount thereof in the maximally stretched state is defined as 100, the stress in the leg cuff first region ST is greater than the stress in the leg cuff second region IT when the elongation amount is 5. On the other hand, when the elongation amount is 100, the stress in the leg cuff second region IT is greater than the stress in the leg cuff first region ST. This relationship can be expressed as a graph shown in FIG. 5.

Note that the "elongation amount" above is defined as follows. When the elongation amount of a leg cuff 24 in its natural state is 0, this means a state in which none of the elastic members included in the leg cuff 24 are stretched and the elastic members are at their minimum length, and in particular, the length of a section of the leg cuff 24 where the outermost leg elastic member 25s is arranged is the shortest. When this length, that is, the natural length of the section of the leg cuff 24 where the outermost leg elastic member 25s is arranged is represented as L1, and the length thereof in the maximally stretched state is represented as L2, the elongation amount at any given length L between L1 and L2 can be expressed as $[(L-L1)/(L2-L1)] \times 100$. Moreover, in the case where the leg cuff 24 is divided into the leg cuff second region IT and the leg cuff first region ST as well, the shortest length L1 of the leg cuff first region ST or the leg cuff second region IT in the natural state is defined as the length when the elongation amount is 0. The length in the maximally stretched state is the length of the leg cuff first region ST and the leg cuff second region IT measured in a state in which the leg elastic members 25 have been removed from the leg cuff first region ST and the leg cuff second region IT.

Figure 5:
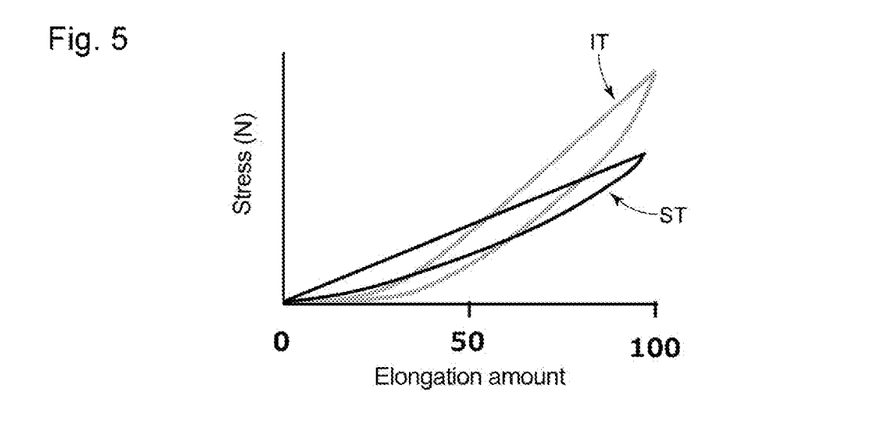
FIG. 5 is a graph showing a relationship between elongation amount and stress, with respect to a leg cuff second region and a leg cuff first region of a leg cuff.

As shown in FIG. 5, when the elongation amount is 5, the stress in the leg cuff first region ST is greater than the stress in the leg cuff second region IT. Then, as the elongation amount increases, both the stress in the leg cuff first region ST and the stress in the leg cuff second region IT increase, but the rate of increase is different between the two regions. Specifically, with respect to the stress in the leg cuff first region ST, the slope of the graph is small, and the rate of increase is low; therefore, even when the elongation amount is increased greatly, the stress does not increase greatly. In contrast, with respect to the stress in the leg cuff second region IT, after the elongation amount is increased to a predetermined value, the slope of the graph increases sharply, and the rate of increase is high; therefore, when the elongation amount is increased greatly, the stress in the leg cuff second region IT also increases greatly. As a result, when the elongation amount takes a specific value, the value of the stress in the leg cuff first region ST and the value of the stress in the leg cuff second region IT are the same, and when the elongation amount is greater than this specific value, the relationship in magnitude between the stress in the leg cuff first region ST and the stress in the leg cuff second region IT is reversed from the previous relationship, and the value of the stress in the leg cuff second region IT becomes greater than the value of the stress in the leg cuff first region ST. In this manner, when the elongation amount is 100, the stress in the leg cuff second region IT is greater than the stress in the leg cuff first region ST.

As a result of the stress in the leg cuff first region ST and the stress in the leg cuff second region IT having such a relationship, the diaper 1 achieves advantageous effects as follows: even when the distance between the diaper 1 and the circumference of the leg of the wearer attempts to change from the wearing state immediately after the diaper 1 is put on due to movements of the wearer, the fit between the circumference of the leg of the wearer and the leg cuff 24 is improved, and the leg cuff 24 is stably kept in contact with the circumference of the leg of the wearer, thus making it unlikely for a gap that may allow liquid leakage to be formed between the leg cuff 24 and the circumference of the leg of the wearer. Moreover, the diaper 1 achieves an advantageous effect of making it unlikely that the leg cuff 24 will form a compression mark on the circumference of the leg of the wearer. This will be described with reference to FIGS. 6 and 7.

Figure 6:
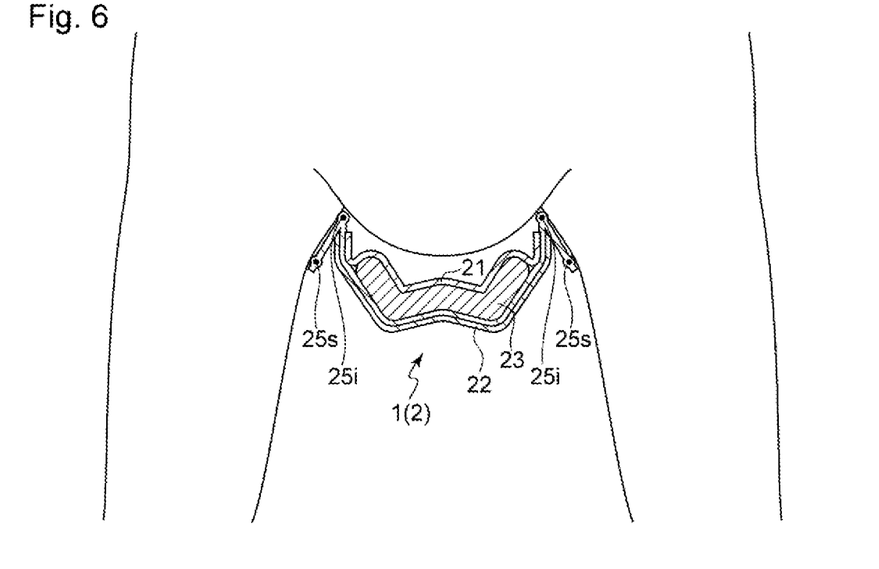
FIG. 6 is a schematic diagram showing a state of a crotch area when the diaper shown in Fig. I is worn by a wearer.

The state shown in FIG. 6 is a state in which the distance between the body and the absorbent assembly 2 is small immediately after the diaper 1 is put on the body. In such a state, the elongation amount of each leg cuff 24 is generally large. As a result, when a comparison is made between the value of the stress in the leg cuff first region ST and the value of the stress in the leg cuff second region IT, the stress in the leg cuff second region IT is greater than the stress in the leg cuff first region ST. Therefore, the leg cuff second region IT attempts to contract more strongly than the leg cuff first region ST, and thus, in the leg cuff 24, as shown in FIG. 6, the leg cuff second region IT, which is the closer one to the absorbent member 23, stands up higher than the leg cuff first region ST toward the skin of the wearer. Accordingly, the leg cuff first region ST can be prevented from protruding into the diaper 1 and reducing the crotch space.

Figure 7:
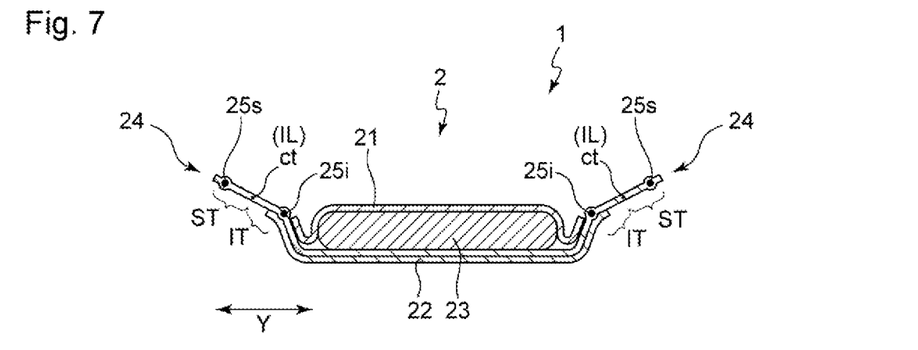
FIG. 7 is a schematic diagram showing a state of the diaper shown in FIG. 1 when the diaper is worn by a wearer.

Next, the state shown in FIG. 7 is a state in which, after the diaper 1 has been put on, the distance between the body of the wearer and the absorbent assembly 2 is increased due to movements of the wearer. In such a state, the elongation amount of each leg cuff 24 is generally small. As a result, when a comparison is made between the value of the stress in the leg cuff first region ST and the value of the stress in the leg cuff second region IT, the stress in the leg cuff first region ST is greater than the stress in the leg cuff second region IT. Accordingly, the leg cuff first region ST attempts to contract more strongly than the leg cuff second region IT. Thus, in the leg cuff 24, as shown in FIG. 7, the leg cuff first region ST, which is farther away from the absorbent member 23 in the width direction Y than the leg cuff second region IT, stands up higher than the leg cuff second region IT toward the skin of the wearer. Therefore, in the leg cuff 24, since the elongation amount of the leg cuff 24 is small, the leg cuff first region ST is in appropriate contact with the leg base that is located outward of the inguinal region of the wearer, and even if the distance between the body of the wearer and the absorbent assembly 2 increases due to movements of the wearer, a gap is unlikely to be formed between the circumference of the leg of the wearer and the leg cuff 24. This effectively prevents the occurrence of liquid leakage and makes it unlikely for a compression mark to be formed on the circumference of the leg of the wearer.

In this manner, with the diaper 1, both in the wearing state immediately after the diaper 1 is put on and in the case where the distance between the diaper 1 and the circumferences of the legs of the wearer attempts to change due to movements of the wearer, the leg cuffs 24 are prevented from protruding into the crotch space and conform to the circumferences of the respective legs of the wearer, and thus a gap that may lead to liquid leakage is unlikely to be formed between the circumferences of the legs of the wearer and the leg cuffs 24. In order to make these effects even more profound, it is preferable that, when the elongation amount is within a range from 6 to 70, or in particular, within a range from 7 to 65, the relationship in magnitude between the stress in the leg cuff first region ST and the stress in the leg cuff second region IT is reversed from the previous relationship. The relationship in magnitude between the stress in the leg cuff first region ST and the stress in the leg cuff second region IT can be suitably adjusted by various means, which will be described later for example.

The stress in the leg cuff first region ST and the stress in the leg cuff second region IT that have been described above are measured in the following manner.

(1) A leg cuff 24 is cut out. Specifically, a section spanning from a position located about 5 mm inward of the innermost leg elastic member 25i to a position located about 5 mm outward of the outermost leg elastic member 25s is cut out as a sample so that the sample includes the innermost leg elastic member 25i and the outermost leg elastic member 25s, and the leg elastic members 25 do not detach even when a stretching operation is performed. The sample is cut out such that the cut-out sample does not include other leg elastic members 25 at the position located about 5 mm inward of the innermost leg elastic member 25i and the position located about 5 mm outward of the outermost leg elastic member 25s. At this time, the distance from the innermost leg elastic member 25i to the cutting line positioned inward thereof and the distance from the outermost leg elastic member 25s to the cutting line positioned outward thereof are set to be equal to each other. The sample is bisected into the leg cuff second region IT and the leg cuff first region ST by the imaginary line IL to prepare measurement specimens.

(2) For each measurement specimen, regions that are located in opposite end portions in the longitudinal direction X of the measurement specimen and include no elastic members are respectively held in chucks of a TENSILON universal testing machine (RTC-1210A) manufactured by ORIENTEC Corporation, with the holding positions being 10 mm from the ends.

(3) Each measurement specimen is pulled in an upward direction at a rate of 300 mm/min until the elongation amount reaches 100, and the stress when the elongation amount during loading is 5 and the stress when the elongation amount is 100 are measured. For both the leg cuff first region ST and the leg cuff second region IT, the wording "when the elongation amount is 100" refers to the time when the measurement specimen has been pulled so that the distance between the chucks is a value obtained by subtracting the holding margins, that is, 20 mm from the length L2 in the maximally stretched state.

In order to, as shown in FIG. 7, make the leg cuff first region ST of the leg cuff 24 stand up higher than the leg cuff second region IT toward the skin of the wearer, make the leg cuff first region ST appropriately come into contact with the leg base of the wearer located outward of the inguinal region, and thereby make it unlikely that a gap is formed between the circumference of the leg of the wearer and the leg cuff 24, it is preferable that, when the leg cuff 24 is in the natural state, the length Ls of the leg cuff first region ST is shorter than the length Li of the leg cuff second region IT. That is to say, it is preferable that Ls<Li. In order to make these effects even more profound, the value of Li/Ls is preferably from 1.01 to 2.00, and more preferably from 1.01 to 1.80.

The lengths Ls and Li are measured in the following manner.

(1) A leg cuff 24 is cut out. The cut-out sample is bisected into the leg cuff second region IT and the leg cuff first region ST by the imaginary line IL passing through the center of the leg cuff 24 to prepare measurement specimens.

(2) Each measurement specimen is straightened out to such an extent that the leg elastic members 25 do not exert a contracting force. At this time, the measurement specimen can be attached to a stand with use of pressure-sensitive adhesive tape or the like.

(3) For each measurement specimen, the length from one end to the other end of the shortest portion of a section of the measurement specimen where the outermost leg elastic member 25s or the innermost leg elastic member 25i is arranged is measured.

(4) The measurement according to (1) to (3) is performed three times, and averages of the three results of measurement in (3) with respect to the lengths of the shortest portions of the measurement specimens in the sections where the outermost leg elastic member 25s and the innermost leg elastic member 25i are respectively arranged are used as Ls and Li.

In order to make the lengths Ls and Li satisfy the above-described relationship, it is preferable that, in the leg cuff 24 for example, out of the leg elastic members 25 and 25, the elongation percentage Ss of the outermost leg elastic member 25s is higher than the elongation percentage Si of the leg elastic member 25 arranged in the leg cuff second region IT. In particular, the value of Ss/Si is preferably from 1.01 to 2.00, and more preferably from 1.01 to 1.80. In order to make Ss greater than Si, the leg elastic member 25 in the leg cuff second region and the outermost leg elastic member 25s can be attached to the leg cuff 24 in a state in which the outermost leg elastic member 25s is stretched to a higher elongation percentage than the innermost leg elastic member 25i in the leg cuff second region IT. Note that, in the case where three or more leg elastic members 25 are arranged in the leg cuff 24, it is preferable that the elongation percentage Ss of the outermost leg elastic member 25s is higher than the elongation percentage Si of every leg elastic member 25 in the leg cuff second region IT, and the elongation percentages of the leg elastic members 25 progressively decrease from the outermost leg elastic member 25s side toward the innermost leg elastic member 25i side. Here, the wording "progressively decrease" means not only a case where the elongation percentages of all of the three or more leg elastic members 25 are different and decrease gradually from the outermost leg elastic member 25s side toward the innermost leg elastic member 25i side, but also a case where the three or more leg elastic members 25 include leg elastic members 25 that are adjacent to each other and have the same elongation percentage, and the elongation percentages decrease in stages from the outermost leg elastic member 25s side toward the innermost leg elastic member 25i side.

The elongation percentages Ss and Si are measured in the following manner.

(1) Each of the leg cuff second region IT and the leg cuff first region ST is stretched to the length of the maximally stretched state and fixed, and the lengths of stretchable regions in which the respective leg elastic members 25 are fixed to the leg cuff 24 with use of an adhesive or the like are measured. The "length of a stretchable region" refers to the distance between fixed ends of each of the leg elastic members 25. The "fixed ends" refers to ends of a leg elastic member 25 that are located in end portions in the longitudinal direction X of the leg elastic member 25 and at positions where the leg elastic member 25 is fixed to the leg cuff 24.

(2) The leg elastic members 25 are each cut along two lateral side end portions extending in the longitudinal direction X of a region in which the leg elastic member 25 is fixed to the leg cuff 24. The leg elastic members 25 are then removed from the leg cuff 24 with use of ethanol or the like.

(3) Each leg elastic member 25 is straightened out to such an extent that a contracting force is not exerted, and the natural length thereof is measured. At this time, the elastic member 25 that has been removed can be attached to a stand with use of pressure-sensitive adhesive tape or the like.

(4) The length of the stretchable region of each of the leg elastic members 25 measured in (1) is divided by the natural length of that leg elastic member 25 measured in (3). Thus, the elongation percentages Ss and Si are calculated.

In order to make the length Li of the leg cuff second region IT in the natural state longer than the length Ls of the leg cuff first region ST in the natural state, or in other words, in order to make the stress Si in the leg cuff second region IT smaller than the stress Ss in the leg cuff first region ST when the elongation amount of the leg cuff 24 is 5, it is preferable that, as shown in FIG. 4, in a cross-sectional view of the diaper 1 taken along the width direction Y, the backsheet 22 extends outward on both sides in the width direction Y past the innermost leg elastic members 25$i$ so that two lateral side edges 22$s$ and 22$s$ extending in the longitudinal direction X of the backsheet 22 are respectively situated in the leg cuff second regions IT. Note that it is preferable that the lateral side edges 22$s$ of the backsheet 22 do not reach the inside of the respective leg cuff first regions ST. In this manner, in each leg cuff second region IT, the backsheet 22 constituting the leg cuff second region IT is also laminated in addition to the leg elastic member 25, and resists against a contracting force when the elongation amount of the leg cuff 24 is small, and therefore, an effect of reducing the stress in the leg cuff second region is obtained.

In order to make the leg cuffs 24 appropriately come into contact with the inguinal region of the wearer irrespective of the distance between the diaper 1 and the body of the wearer, it is preferable that, out of the leg elastic members 25 and 25 of each leg cuff 24, the modulus Mi of the innermost leg elastic member 25$i$ in the leg cuff second region IT is higher than the modulus Ms of the outermost leg elastic member 25$s$. It is more preferable that the modulus of every leg elastic member 25 in the leg cuff second region IT is higher than the modulus Ms of the outermost leg elastic member 25$s$. The "modulus" refers to tensile stress that is a resistive force exerted by an object against an external force in order to keep its original shape. When Ms<Mi, the modulus Mi of the innermost leg elastic member 25$i$ can be easily increased in a region of the leg cuff 24 where the elongation amount is large. From this point of view, the value of Mi/Ms is preferably from 1.01 to 2.00, and more preferably from 1.01 to 1.80. In order to make Mi greater than Ms, a method may be adopted for example in which an isoprene rubber that exhibits high resilience is used as the innermost leg elastic member 25$i$ in the leg cuff second region IT, and a styrene-butadiene rubber that exhibits low resilience is used as the outermost leg elastic member 25$s$ in the leg cuff first region ST.

The above-described "modulus" is defined as follows. The individual leg elastic members 25 included in the leg cuff 24 are removed from the leg cuff 24. The natural length of each of the removed leg elastic members 25 is represented as LE1. Moreover, the length that is double the length LE1 is represented as LE2. Furthermore, the stress when the leg elastic member 25 is pulled to a length LE1.5 that is 1.5 times the length LE1 is represented as SE1.5, and the stress when the leg elastic member 25 is pulled to the length LE2 is represented as SE2. Then, the values of the ratio between SE1.5 and SE2, (SE2)/(SE1.5), are used as indicators of the moduli Mi and Ms.

The moduli Mi and Ms are measured in the following manner.

(1) The leg elastic members 25 are removed from a leg cuff 24 with use of ethanol or the like.

(2) Each of the leg elastic members 25 is straightened out to such an extent that a contracting force is not exerted. Marks are made at positions 10 mm inward of the opposite end portions of the leg elastic member 25 so as to leave holding margins of 10 mm, and the natural length (LE1) of the stretchable region between the marks is measured.

(3) The leg elastic member 25 is gripped in a TENSILON universal testing machine (RTC-1210A) manufactured by ORIENTEC Corporation, with the gripping positions being 10 mm from the respective ends of the leg elastic member 25, and pulled in an upward direction at a rate of 300 mm/min until the inter-chuck distance becomes double (LE2) the natural length of the stretchable region of the leg elastic member 25, and the stress at that time is measured (SE2).

(4) The leg elastic member 25 is pulled to 1.5 times (LE1.5) the natural length of the stretchable region thereof, and the stress at that time is measured (SE1.5). Then, the ratio of SE2 to SE1.5, that is, (SE2)/(SE1.5) is calculated.

In the above measurement, the natural lengths (LE1) of the stretchable regions of the individual leg elastic members 25 may be set to be a desired uniform length, and, for example, in the case where the natural lengths (LE1) of the stretchable regions are set to be 70 mm, each sample can be cut out so that the length of the leg elastic member 25 including the gripping margins is 90 mm, and stretched, with both end portions of a length of 10 mm being gripped, until the inter-chuck distance changes from the natural length (LE1) of the stretchable region of the leg elastic member 25, that is, 70 mm, to a length (LE2) that is double the natural length (LE1), that is, 140 mm.

As shown in FIG. 6, in order to make the leg cuff second region IT of the leg cuff 24 stand up higher than the leg cuff first region ST toward the skin of the wearer, prevent the leg cuff 24 from protruding into the inside of the diaper 1, and secure a crotch space, it is preferable that, out of the leg elastic members 25 and 25, the thickness Di of the innermost leg elastic member 25$i$ in the leg cuff second region IT is greater than the thickness Ds of the outermost leg elastic member 25$s$ arranged in the leg cuff first region ST. From this point of view, the value of Di/Ds is preferably from 1.30 to 3.00, and more preferably from 1.50 to 2.60. Note that, in the case where three or more leg elastic members 25 are arranged in the leg cuff 24, it is preferable that every leg elastic member 25 arranged in the leg cuff second region IT has a greater thickness than the outermost leg elastic member 25$s$ in the leg cuff first region ST. Furthermore, all of the leg elastic members 25 of the leg cuff 24 may have different thicknesses, and in that case, it is preferable that the thicknesses progressively increase from the outermost leg elastic member 25$s$ side toward the innermost leg elastic member 25$i$ side. Here, the wording "progressively increase" means not only a case where all of the three or more leg elastic members 25 have different thicknesses, and the thicknesses increase gradually from the outermost leg elastic member 25$s$ side toward the innermost leg elastic member 25$i$ side, but also a case where the three or more leg elastic members 25 include leg elastic members 25 that are adjacent to each other and have the same thickness, and the thicknesses increase in stages from the outermost leg elastic member 25$s$ side toward the innermost leg elastic member 25$i$ side.

In order for the pair of leg cuffs 24 and 24 to prevent the formation of a gap between the wearer and the leg cuffs 24, it is preferable that, in each of the leg cuffs 24 extending from the front portion 1A to the rear portion 1C, as shown in FIG. 2, at least the fixed end portions 25*a* of the leg elastic members 25, the fixed end portions 25*a* being fixed to the leg cuff 24 on the front portion 1A side in the longitudinal direction X, extend in the longitudinal direction X into the front outer cover 3A, which is included in the front portion 1A. It is more preferable that, in addition to the fixed end portions 25*a* on the front portion 1A side extending into the front outer cover 3A, fixed end portions 25*c* on the rear portion 1C side in the longitudinal direction X extend in the longitudinal direction X into the rear outer cover 3C, which is included in the rear portion 1C. In order to make the above-described effect even more profound, it is preferable that the fixed end portions 25*a* of the leg elastic members 25 that are fixed to the leg cuff 24 are located closer to the waist opening WH, into which the waist of the wearer is to be inserted, than either the below-waist elastic member 33 that are arranged in the front outer cover 3A stretched in the width direction Y or the below-waist elastic member 33 that are arranged in the rear outer cover 3C stretched in the width direction Y. It is more preferable that the fixed end portions 25*a* are located closer to the waist opening WH, into which the waist of the wearer is to be inserted, than the below-waist elastic member 33 arranged in the front outer cover 3A and the below-waist elastic member 33 arranged in the rear outer cover 3C. Here, the meaning of "the fixed end portions 25*a* are located closer to the waist opening WH than the below-waist elastic members 33" includes a case in which the fixed end portions 25*a* at least overlap the below-waist elastic members 33 in the thickness direction.

In order to prevent the formation of a gap between the wearer and the leg cuffs 24 and 24, as shown in FIGS. 2 to 4, the diaper 1 includes the pair of leak-proof cuffs 28 and 28 that are located inward of the pair of leg cuffs 24 and 24. In order to improve the standability of the pair of leak-proof cuffs 28 and 28 in the crotch portion 1B and prevent the formation of a gap even further, it is preferable that an end portion 28*a* on the front portion 1A side in the longitudinal direction X and an end portion 28*c* on the rear portion IC side, of each leak-proof cuff 28 are fixed to the skin-facing surface of the topsheet 21 that is located on the absorbent member 23. The leak-proof cuffs 28 are formed by, for example, obtaining sheet members in each of which a single sheet for constituting a leak-proof cuff 28 is folded in half, and a leak-proof cuff elastic member 29 in a stretched state is arranged between the two halves of the half-folded sheet and fixed thereto with use of an adhesive or the like, and fixing the obtained sheet members respectively to two lateral side regions extending in the longitudinal direction X of the absorbent assembly 2 via fixed portions formed by an adhesive or the like. The fixed portions of the thus formed leak-proof cuffs 28 are arranged on the skin-facing surface of the topsheet 21 in the respective lateral side regions of the absorbent assembly 2 and extend from the front portion 1A to the rear portion IC along the longitudinal direction X. Note that instead of folding a single sheet for constituting a leak-proof cuff 28 in half, it is also possible to form the leak-proof cuffs 28 by obtaining sheet members in each of which a leak-proof cuff elastic member 29 in a stretched state is arranged on one the two faces of the sheet and fixed thereto using an adhesive or the like, and fixing the thus obtained sheet members to the respective lateral side regions of the absorbent assembly 2 with use of an adhesive or the like.

It is more preferable that, in the crotch portion 1B when the diaper is worn, the pair of leak-proof cuffs 28 and 28 are arranged inward of the pair of leg cuffs 24 and 24, because this configuration makes it possible to suppress spreading of excreta in the width direction Y and thereby prevent leakage. At this time, in order to prevent the leg cuffs 24 from going over the leak-proof cuffs 28 and protruding into the crotch portion 1B, it is preferable that, as shown in FIG. 4, in a cross-sectional view of the diaper 1 taken along the width direction Y, the distance K24 that is the distance between the lateral side edge of each lateral side portion 23*s* extending in the longitudinal direction X of the absorbent member 23 and the corresponding innermost leg elastic member 25*i* is shorter than the distance K28 that is the distance between the lateral side edge of that lateral side portion 23*s* of the absorbent member 23 and the leak-proof cuff elastic member 29 that is the farthest away from the lateral side edge (the closest to a free end portion). That is to say, it is preferable that K24<K28. In order to make this effect even more profound, the value of K24/K28 is preferably from 0.10 to 0.99, and more preferably from 0.25 to 0.99.

The lengths K24 and K28 are measured in the following manner.

(1) The leak-proof cuff elastic member 29 and the leg elastic members 25 are straightened out to such an extent that a contracting force is not exerted, and a position at which the leg cuff 24 and the lateral side edge of the lateral side portion 23S extending in the longitudinal direction X of the absorbent member 23 overlap in the thickness direction, as well as a position at which the leak-proof cuff 28 and that lateral side edge of the absorbent member 23 overlap in the thickness direction are marked.

(2) Straight lines that are parallel to the width direction Y are drawn from the positions marked in (1).

(3) The distance along the straight line from the position at which the straight line crosses the innermost leg elastic member 25*i* to the above-described marked position at which the leg cuff 24 and the lateral side edge of the absorbent member 23 overlap is used as the distance K24. Moreover, the distance along the straight line from the position at which the straight line crosses the leak-proof cuff elastic member 29 to the above-described marked position at which the leak-proof cuff 28 and the lateral side edge of the absorbent member 23 overlap is used as the distance K28.

In order to prevent, in the crotch portion 1B when the diaper is worn, the leg cuffs 24 from going over the leak-proof cuffs 28 and protruding into the crotch portion 1B, it is preferable that, as is the case with the leg cuffs 24, when the elongation amount of the leak-proof cuffs 28 in a natural state is defined as 0, and the elongation amount thereof in a maximally stretched state is defined as 100, the stress in the leak-proof cuffs 28 when the elongation amount is 100 is greater than the stress in the leg cuff second regions IT when the elongation amount is 100.

Note that the above-described elongation amount of the leak-proof cuffs 28 is defined as follows. When the natural length of a leak-proof cuff 28 in a state in which none of the leak-proof cuff elastic members 29 included in the leak-proof cuff 28 are stretched and the leak-proof cuff elastic members 29 are at their minimum length is represented as L3, and the length thereof in the maximally stretched state is represented as L4, the elongation amount at any given length L5 between L3 and L4 can be expressed as (L5−L3)/)(L4−L3)×100. The length in the maximally stretched state refers to the length of the leak-proof cuff 28 itself that is measured in a state in which the leak-proof cuff elastic members 29 are removed from the leak-proof cuff 28.

The stress in each leak-proof cuff 28 is measured in the following manner.

(1) The leak-proof cuff 28 is cut out. Specifically, a measurement specimen is prepared by cutting out the leak-proof cuff 28 at positions about 3 mm from two lateral side edges extending in the longitudinal direction X of the leak-proof cuff elastic member 29 so that the measurement specimen includes nothing other than the leak-proof cuff elastic member 29.

(2) For the measurement specimen, regions that are located in opposite end portions in the longitudinal direction X of the leak-proof cuff 28 and include no leak-proof cuff elastic member 29 are respectively held in chucks of a TENSILON universal testing machine (RTC-1210A) manufactured by ORIENTEC Corporation, with the holding positions being 10 mm from the respective ends.

(3) The measurement specimen is pulled in an upward direction at a rate of 300 mm/min until the elongation amount reaches 100, and the stress when the elongation amount is 100 is measured. The wording "when the elongation amount is 100" refers to the time when the measurement specimen has been pulled so that the distance between the chucks is a value obtained by subtracting the holding margins, that is, 20 mm from the length L2 in the maximally stretched state.

In order for the pair of leg cuffs 24 and 24 to prevent the formation of a gap between the wearer and the leg cuffs 24, it is preferable that, in a planar view such as that shown in FIG. 2, in each of the leg cuffs 24 extending from the front portion 1A to the rear portion 1C, either the fixed end portions 25*a* on the front portion 1A side in the longitudinal direction X or the fixed end portions 25*c* on the rear portion 1C side, at which the leg elastic members 25 are fixed to the leg cuff 24, are located closer to the waist opening WH, which is an end portion in the longitudinal direction X of the diaper 1, than the leak-proof cuff fixed end portion 28*a* on the front portion LA side in the longitudinal direction X or the leak-proof cuff fixed end portion 28*c* on the rear portion 1C side, of each leak-proof cuff 28, where the leak-proof cuff elastic member 29 is fixed to the leak-proof cuff 28. It is more preferable that the fixed end portions 25*a* on the front portion 1A side in the longitudinal direction X and the fixed end portions 250 on the rear portion 1C side, of the leg elastic members 25, are respectively located closer to the waist opening WH of the diaper I than the leak-proof cuff fixed end portion 29*a* on the front portion IA side in the longitudinal direction X and the leak-proof cuff fixed end portion 29*c* on the rear portion 1C side, of the leak proof cuff elastic member 29. In this manner, a comparison of the lengths of substantial stretchable regions stretchable regions is made by comparing the positions of the fixed end portions 25*a* and 25*c* of the leg elastic members 25 with the positions of the leak-proof cuff fixed end portions 28a and 28*c* of the leak-proof cuff elastic member 29, rather than comparing the lengths of the leg elastic members 25 with the length of the leak-proof cuff elastic member 29.

Figure 8:
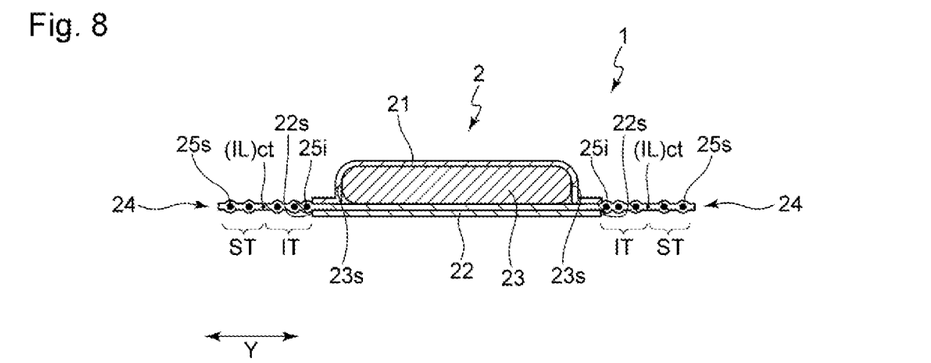
FIG. 8 is a cross-sectional view (view corresponding to FIG. 4) schematically showing a cross section, taken along a lateral direction, of a disposable diaper according to another embodiment of the absorbent article of the present invention.

FIG. 8 shows another embodiment of the present invention. In the other embodiment, which will be described below, components that are different from those of the above-described diaper 1 will be described primarily, and like components are denoted by like reference numerals and their descriptions are omitted. Descriptions of the above-described diaper 1 are appropriately applied to those components that will not be described. The diaper 1 shown in FIG. 8 also achieves similar effects to those of the diaper 1 shown in FIGS. 1 to 4.

The diaper 1 shown in FIG. 8 differs from the above-described diaper 1 shown in FIGS. 1 to 4 in terms of the number of leg elastic members 25 constituting the leg cuffs 24. Specifically, in the diaper 1 shown in FIG. 8, five leg elastic members 25 are arranged in each leg cuff 24. The diaper 1 shown in FIG. 8 has, in the maximally stretched state, two leg elastic members 25 and 25 in the leg cuff first region ST that extends from the imaginary line IL, which passes through the center ct in the width direction between the outermost leg elastic member 25*s* and the innermost leg elastic member 25*i*, up to and including the outermost leg elastic member 25*s*, and three leg elastic members 25, 25 and 25 in the leg cuff second region IT that extends from the imaginary line IL up to and including the innermost leg elastic member 25*i*. If, as described above, the number of leg elastic members 25 arranged in the leg cuff second region IT is greater than the number of leg elastic members 25 arranged in the leg cuff first region ST, in a state in which the distance between the body and the absorbent assembly 2 is small immediately after the diaper 1 is put on, or in other words, in a state in which the leg cuffs 24 generally have a large elongation amount, the leg cuff second regions IT of the leg cuffs 24 are likely to stand up higher than the leg cuff first regions ST toward the skin of the wearer. Thus, the leg cuff second regions IT are positioned so as to appropriately come into contact with the inguinal region of the wearer, and the leg cuff first regions ST are prevented from protruding into the crotch space. Accordingly, the occurrence of liquid leakage is effectively prevented.

In order to make the above-described effects even more profound, it is preferable that the intervals between the three leg elastic members 25, 25 and 25 in the leg cuff second region IT are individually equal to the interval between the two leg elastic members 25 and 25 in the leg cuff first region ST or shorter than the interval between the two leg elastic members 25 and 25 in the leg cuff first region ST. If, as described above, the intervals between the three leg elastic members 25, 25 and 25 in the leg cuff second region IT are short, the three leg elastic members 25, 25 and 25 simulatively exhibit similar stretching and contracting behavior to that of a single leg elastic member 25, and thus, the leg cuff second region IT can be contracted strongly. From this point of view, it is preferable that, when three or more leg elastic members 25 are arranged in the leg cuff first region ST, the interval between the leg elastic members 25 and 25 in the leg cuff second region IT is shorter than any of the intervals between those leg elastic members 25 and 25. Moreover, it is more preferable that, when three or more leg elastic members 25 are arranged in the leg cuff second region IT, the intervals between those leg elastic members 25 and 25 progressively decrease toward the absorbent member 23 side.

Although the present invention has been described above based on the embodiments, the present invention is not limited to the foregoing embodiments, and changes may be made thereto as appropriate.

For example, in the foregoing embodiments, the absorbent article of the present invention is applied to a pull-on disposable diaper, but instead the present invention may be applied to an open type disposable diaper. In addition, the present invention may also be applied to absorbent articles other than disposable diapers, such as sanitary napkins and incontinence pads for example.

Moreover, the diaper 1 shown in FIGS. 1 to 3 has a form in which the outer cover 3 is divided into the front outer cover 3A located in the front portion 1A and the rear outer cover 3C located in the rear portion 1C, and the diaper 1 is formed by bridging and fixing the absorbent assembly 2 between the two sheet members, but instead, the diaper 1 may have a form in which the outer cover 3 has a continuous shape spanning from the front portion 1A to the rear portion 1C via the crotch portion 1B, and the diaper 1 is formed by fixing the absorbent assembly 2 to a central portion of that outer cover In the case of a pull-on disposable diaper with such a form, the leg cuffs 24 including the leg elastic members 25 may be arranged in the outer cover.

With regard to the foregoing embodiments of the present invention, additional remarks below will be further disclosed.

<1> An absorbent article including a liquid-retentive absorbent member, and a leg cuff extending outward in a width direction from each of two lateral side portions of the absorbent member that extend in a longitudinal direction, the leg cuff extending along the lateral side portion, wherein two or more leg elastic members extending in the longitudinal direction are arranged in the leg cuff in a stretched state; the leg cuff is divided, by an imaginary line extending in the longitudinal direction through a center in the width direction between, out of the leg elastic members, an outermost leg elastic member located farthest outward in the width direction and an innermost leg elastic member located farthest inward in the width direction, into a leg cuff first region that extends from the imaginary line up to and including the outermost leg elastic member and a leg cuff second region that extends from the imaginary line up to and including the innermost leg elastic member; and when an elongation amount of the leg cuff first region and the leg cuff second region in a natural state is defined as 0, and the elongation amount thereof in a maximally stretched state is defined as 100, stress in the leg cuff first region is greater than stress in the leg cuff second region when the elongation amount is 5, and stress in the leg cuff second region is greater than stress in the leg cuff first region when the elongation amount is 100.

<2> The absorbent article as set forth in clause <1>, wherein, in a natural state of the leg cuff, a section of the leg cuff first region where the outermost leg elastic member is arranged has a shorter length than a section of the leg cuff second region where the innermost leg elastic member is arranged.

<3> The absorbent article as set forth in clause <1> or <2>, wherein the outermost leg elastic member has a higher elongation percentage than the innermost leg elastic member.

<4> The absorbent article as set forth in any one of clauses <1> to <3>, wherein the innermost leg elastic member has a higher modulus than the outermost leg elastic member.

<5> The absorbent article as set forth in any one of clauses <1> to <4>, wherein the innermost leg elastic member has a greater thickness than the outermost leg elastic member.

<6> The absorbent article as set forth in any one of clauses <1> to <5>, wherein three or more of the leg elastic members are arranged in the leg cuff, and a greater number of the leg elastic members are arranged in the leg cuff second region than in the leg cuff first region.

<7> The absorbent article as set forth in any one of clauses <1> to <6>, wherein a plurality of the leg elastic members are arranged in each of the leg cuff first region and the leg cuff second region, and an interval between the leg elastic members in the leg cuff second region is equal to an interval between the leg elastic members in the leg cuff first region or shorter than the interval between the leg elastic members in the leg cuff first region.

<8> The absorbent article as set forth in any one of clauses <1> to <7>, wherein a relationship in magnitude between stress in the leg cuff first region and stress in the leg cuff second region is reversed when the elongation amount is within a range from 6 to 70.

<9> The absorbent article as set forth in any one of clauses <1> to <8>, wherein three or more of the leg elastic members are arranged in the leg cuff, the outermost leg elastic member has a higher elongation percentage than every elastic member arranged in the leg cuff second region, and the elongation percentages of the leg elastic members progressively decrease from the outermost leg elastic member side toward the innermost leg elastic member side.

<10> The absorbent article as set forth in any one of clauses <1> to <9>, wherein three or more of the leg elastic members are arranged in the leg cuff, every elastic member arranged in the leg cuff second region has a greater thickness than the outermost leg elastic member, and the thicknesses of the leg elastic members progressively increase from the outermost leg elastic member side toward the innermost leg elastic member side.

<11> The absorbent article as set forth in any one of clauses <1> to <10>, wherein a sparingly-liquid permeable backsheet is arranged on a non-skin-facing surface of the absorbent member, and in a cross-sectional view of the absorbent article taken along the width direction, the backsheet extends so that two lateral side edges thereof extending in the longitudinal direction are situated in respective ones of the leg cuff second regions.

<12> The absorbent article as set forth in any one of clauses <1> to <11>, wherein the absorbent article is a disposable diaper, the absorbent article includes a below-waist portion that is placed below the waist of a wearer when the absorbent article is worn, the below-waist portion being divided into a front portion and a rear portion that are placed on an anterior side and a posterior side, respectively, of the wearer when the absorbent article is worn, the leg cuff is arranged spanning between the front portion and the rear portion, and fixed end portions of the leg elastic members where the leg elastic members are fixed to the leg cuff extend into at least the front portion.

<13> The absorbent article as set forth in any one of clauses <1> to <12>, wherein the absorbent article is a disposable diaper, the absorbent article comprises a below-waist portion that is placed below the waist of a wearer when the absorbent article is worn, the below-waist portion being divided into a front portion and a rear portion that are placed on an anterior side and a posterior side, respectively, of the wearer when the absorbent article is worn, a below-waist elastic member arranged in a state of being stretched in the width direction is arranged in each of the front portion and the rear portion, the leg cuff is arranged spanning between the front portion and the rear portion, and fixed end portions of the leg elastic members where the leg elastic members are fixed to the leg cuff are located closer to a waist opening into which the waist of the wearer is to be inserted than either of the below-waist elastic member arranged in the front portion and the below-waist elastic member arranged in the rear portion.

<14> The absorbent article as set forth in any one of clauses <1> to <13>, wherein the absorbent article comprises a leak-proof cuff located inward of the leg cuff in the width direction, the leak-proof cuff extending along the lateral side portion of the absorbent member, one or more leak-proof cuff elastic members extending in the longitudinal direction are arranged in the leak-proof cuff while being stretched, a liquid permeable topsheet is arranged on a skin-facing surface of the absorbent member, and two end portions of the leak-proof cuff in the longitudinal direction are fixed to a skin-facing surface of the topsheet located on the absorbent member.

<15> The absorbent article as set forth in clause <14>, wherein, in a cross-sectional view of the absorbent article taken along the width direction, a distance between the lateral side edge of the lateral side portion of the absorbent member and the innermost leg elastic member is shorter than a distance between the lateral side edge of the lateral side portion of the absorbent member and a leak-proof cuff elastic member, out of the leak-proof cuff elastic members, that is located farthest away from the lateral side edge toward a free end portion of the leak-proof cuff.

<16> The absorbent article as set forth in clause <14> or <15>, wherein, when the elongation amount of the leak-proof cuff in a natural state is defined as 0, and the elongation amount thereof in a maximally stretched state is defined as 100, stress in the leak-proof cuff is greater than stress in the leg cuff second region when the elongation amounts of the leg cuff second region and the leak-proof cuff are 100.

<17> The absorbent article as set forth in any one of clauses <14> to <16>, wherein fixed end portions of the leg elastic members where the leg elastic members are fixed to the leg cuff are located closer to an end portion in the longitudinal direction of the absorbent article than a leak-proof cuff fixed end portion where the leak-proof cuff elastic members are fixed to the leak-proof cuff.

<18> The absorbent article as set forth in any one of clauses <14> to <17>, wherein, in a cross-sectional view of the absorbent article taken along the width direction, the value of the ratio (K24/K28) of a distance K24 that is the distance between the lateral side edge of the lateral side portion extending in the longitudinal direction of the absorbent member and the innermost leg elastic member to a distance K28 that is the distance between the lateral side edge of the lateral side portion of the absorbent member and the leak-proof cuff elastic member that is the farthest away from the lateral side edge (the closest to the free end portion) is preferably from 0.10 to 0.99, and more preferably from 0.25 to 0.99.

<19> The absorbent article as set forth in any one of clauses <14> to <18>, wherein it is more preferable that fixed end portions on the front portion side and fixed end portions on the rear portion side of the leg elastic members in the longitudinal direction X are located closer to the waist opening WH into which the waist of the wearer is to be inserted than a leak-proof cuff fixed end portion on the front portion side and a leak-proof cuff fixed end portion on the rear portion side, respectively, of each leak-proof cuff elastic member in the longitudinal direction.

<20> The absorbent article as set forth in any one of clauses <1> to <19>, wherein, when the elongation amount of the leg cuff first region and the leg cuff second region in the natural state is defined as 0, and the elongation amount thereof in the maximally stretched state is defined as 100, it is preferable that a relationship in magnitude between stress in the leg cuff first region and stress in the leg cuff second region is reversed from the previous relationship when the elongation amount is within a range from 6 to 70, or in particular, within a range from 7 to 65.

<21> The absorbent article as set forth in any one of clauses <1> to <20>, wherein the ratio (Li/Ls) of the value of the length Li of the leg cuff second region to the value of the length Ls of the leg cuff first region is preferably from 1.01 to 2.00, and more preferably from 1.01 to 1.80.

<22> The absorbent article as set forth in any one of clauses <1> to <21>, wherein the ratio (Ss/Si) of the value of the elongation percentage Ss of the outermost leg elastic member to the value of elongation percentage Si of the leg elastic member arranged in the leg cuff second region is preferably from 1.01 to 2.00, and more preferably from 1.01 to 1.80.

<23> The absorbent article as set forth in any one of clauses <1> to <22>, wherein the ratio (Mi/Ms) of the value of the modulus Ms of the outermost leg elastic member to the value of the modulus Mi of the innermost leg elastic member in the leg cuff second region is preferably from 1.01 to 2.00, and more preferably from 1.01 to 1.80.

<24> The absorbent article as set forth in any one of clauses <1> to <23>, wherein it is preferable that every leg elastic member in the leg cuff second region has a higher modulus than the modulus Ms of the outermost leg elastic member.

<25> The absorbent article as set forth in any one of clauses <1> to <24>, wherein the ratio (Di/Ds) of the thickness Di of the innermost leg elastic member in the leg cuff second region to the thickness Ds of the outermost leg elastic member in the leg cuff first region ST is preferably from 1.30 to 3.00, and more preferably from 1.50 to 2.60.

<26> The absorbent article as set forth in any one of clauses <1> to <25>, wherein it is more preferable that a fixed end portion of the leg elastic member fixed to the leg cuff on the front portion side in the longitudinal direction extends in the longitudinal direction into a front outer cover that is included in the front portion, and a fixed end portion of the leg elastic member fixed to the leg cuff on the rear portion side in the longitudinal direction extends in the longitudinal direction into a rear outer cover that is included in the rear portion.

<27> The absorbent article as set forth in clause <26>, wherein it is preferable that the fixed end portions of the leg elastic members that are fixed to the leg cuff are located closer to the waist opening into which the waist of the wearer is to be inserted than the below-waist elastic member arranged in the front outer cover and the below-waist elastic member arranged in the rear outer cover, respectively.

<28> The absorbent article as set forth in any one of clauses <1> to <27>, wherein it is preferable that intervals between three of the leg elastic members in the leg cuff second region are shorter than an interval between leg elastic members in the leg cuff first region.

<29> The absorbent article as set forth in any one of clauses <1> to <28>, wherein, when three or more of the leg elastic members are arranged in the leg cuff second region, it is more preferable that intervals between the leg elastic members 25 and 25 progressively decrease toward the absorbent member 23 side.

INDUSTRIAL APPLICABILITY

As described in detail above, according to the present invention, (1) the leg cuffs 28 immediately after the absorbent article is put on are prevented from protruding into the crotch portion 1B and reducing the hydrophilic width (area in which urine can be absorbed); (2) even in a state in which the distance between the diaper 1 and the circumferences of the legs of the wearer changes due to movements of the wearer and causes the formation of a crotch space, the leg cuffs 28 conform to the circumferences of the legs of the wearer without leaving any gap and thereby can prevent leakage; and (3) the leg cuffs are unlikely to form a compression mark on the circumferences of the legs of the wearer while the absorbent article is worn.

As described above, the effects (1) to (3) that have conventionally been difficult to combine can be achieved.

The invention claimed is:

1. An absorbent article comprising a liquid-retentive absorbent member, and a leg cuff extending outward in a width direction from each of two lateral side portions of the absorbent member that extend in a longitudinal direction, the leg cuff extending along the lateral side portion,
   wherein two or more leg elastic members extending in the longitudinal direction are arranged in the leg cuff in a stretched state,
   the leg cuff is divided, in a maximally stretched state, by an imaginary line extending in the longitudinal direction through a center in the width direction between the leg elastic members, an outermost leg elastic member located farthest outward in the width direction and an innermost leg elastic member located farthest inward in the width direction, into a leg cuff first region that extends from the imaginary line up to and comprising the outermost leg elastic member and a leg cuff second region that extends from the imaginary line up to and comprising the innermost leg elastic member, and
   when an elongation amount of the leg cuff first region and the leg cuff second region in a natural state is defined as 0, and the elongation amount thereof in a maximally stretched state is defined as 100,
   stress in the leg cuff first region is greater than stress in the leg cuff second region when the elongation amount is 5, and
   stress in the leg cuff second region is greater than stress in the leg cuff first region when the elongation amount is 100,
   wherein, in a natural state of the leg cuff, a section of the leg cuff first region where the outermost leg elastic member is arranged has a shorter length than a section of the leg cuff second region where the innermost leg elastic member is arranged,
   wherein a relationship in magnitude between stress in the leg cuff first region and stress in the leg cuff second region is reversed when the elongation amount is within a range from 6 to 70, and
   wherein the elongation percentage Ss of the outermost leg elastic member is higher than the elongation percentage Si of the innermost leg elastic member arranged in the leg cuff second region, and
   a value of Ss/Si of the elongation percentage Ss of the outermost leg elastic member to the elongation percentage Si of the innermost leg elastic member arranged in the leg cuff second region is from 1.01 to 2.00.

2. The absorbent article according to claim 1, wherein the innermost leg elastic member has a higher modulus than the outermost leg elastic member.

3. The absorbent article according to claim 1, wherein the innermost leg elastic member has a greater thickness than the outermost leg elastic member.

4. The absorbent article according to claim 1, wherein three or more of the leg elastic members are arranged in the leg cuff, and
a greater number of the leg elastic members are arranged in the leg cuff second region than in the leg cuff first region.

5. The absorbent article according to claim 1, wherein a plurality of the leg elastic members are arranged in each of the leg cuff first region and the leg cuff second region, and
an interval between the leg elastic members in the leg cuff second region is equal to an interval between the leg elastic members in the leg cuff first region or shorter than the interval between the leg elastic members in the leg cuff first region.

6. The absorbent article according to claim 1,
wherein three or more of the leg elastic members are arranged in the leg cuff, the outermost leg elastic member has a higher elongation percentage than every elastic member arranged in the leg cuff second region, and
the elongation percentages of the leg elastic members progressively decrease from the outermost leg elastic member side toward the innermost leg elastic member side.

7. The absorbent article according to claim 1,
wherein three or more of the leg elastic members are arranged in the leg cuff,
every elastic member arranged in the leg cuff second region has a greater thickness than the outermost leg elastic member, and
the thicknesses of the leg elastic members progressively increase from the outermost leg elastic member side toward the innermost leg elastic member side.

8. The absorbent article according to claim 1,
wherein a sparingly liquid permeable backsheet is arranged on a non-skin-facing surface of the absorbent member, and
in a cross-sectional view of the absorbent article taken along the width direction, the backsheet extends so that two lateral side edges thereof extending in the longitudinal direction are situated in respective ones of the leg cuff second regions.

9. The absorbent article according to claim 1,
wherein the absorbent article is a disposable diaper,
the absorbent article comprises a below-waist portion that is placed below the waist of a wearer when the absorbent article is worn, the below-waist portion being divided into a front portion and a rear portion that are placed on an anterior side and a posterior side, respectively, of the wearer when the absorbent article is worn,
the leg cuff is arranged spanning between the front portion and the rear portion, and
fixed end portions of the leg elastic members where the leg elastic members are fixed to the leg cuff extend into at least the front portion.

10. The absorbent article according to claim 1,
wherein the absorbent article is a disposable diaper,
the absorbent article comprises a below-waist portion that is placed below the waist of a wearer when the absorbent article is worn, the below-waist portion being divided into a front portion and a rear portion that are placed on an anterior side and a posterior side, respectively, of the wearer when the absorbent article is worn,
a below-waist elastic member arranged in a state of being stretched in the width direction is arranged in each of the front portion and the rear portion,
the leg cuff is arranged spanning between the front portion and the rear portion, and
fixed end portions of the leg elastic members where the leg elastic members are fixed to the leg cuff are located closer to a waist opening into which the waist of the wearer is to be inserted than either of the below-waist elastic member arranged in the front portion or the below-waist elastic member arranged in the rear portion.

11. The absorbent article according to claim 1,
wherein the absorbent article comprises a leak-proof cuff located inward of the leg cuff in the width direction, the leak-proof cuff extending along the lateral side portion of the absorbent member,
one or more leak-proof cuff elastic members extending in the longitudinal direction are arranged in the leak-proof cuff in a stretched state,
a liquid permeable topsheet is arranged on a skin-facing surface of the absorbent member, and
two end portions of the leak-proof cuff in the longitudinal direction are fixed to a skin-facing surface of the topsheet located on the absorbent member.

12. The absorbent article according to claim 11,
wherein, in a cross-sectional view of the absorbent article taken along the width direction, a distance between the lateral side edge of the lateral side portion of the absorbent member and the innermost leg elastic member is shorter than a distance between the lateral side edge of the lateral side portion of the absorbent member and a leak-proof cuff elastic member that is located farthest away from the lateral side edge toward a free end portion of the leak-proof cuff.

13. The absorbent article according to claim 11,
wherein, when the elongation amount of the leak-proof cuff in a natural state is defined as 0, and the elongation amount thereof in a maximally stretched state is defined as 100, stress in the leak-proof cuff is greater than stress in the leg cuff second region when the elongation amounts of the leg cuff second region and the leak-proof cuff are 100.

14. The absorbent article according to claim 11,
wherein fixed end portions of the leg elastic members where the leg elastic members are fixed to the leg cuff are located closer to an end portion in the longitudinal direction of the absorbent article than a leak-proof cuff fixed end portion where the leak-proof cuff elastic members are fixed to the leak-proof cuff.

15. The absorbent article according to claim 1, wherein a relationship in magnitude between stress in the leg cuff first region and stress in the leg cuff second region is reversed when the elongation amount is within a range from 7 to 65.

16. The absorbent article according to claim 1, wherein in a natural state, a value of Ls/Li of the length Ls of the leg cuff first region to the length Li of the leg cuff second region is from 1.01 to 2.00.

17. The absorbent article according to claim 1, the modulus Mi of the innermost leg elastic member in the leg cuff second region is higher than the modulus Ms of the outermost leg elastic member in the first region, and
a value Mi/Ms of the modulus Mi of the innermost leg elastic member in the leg cuff second region to the modulus Ms of the outermost leg elastic member in the first region is from 1.01 to 2.0.

* * * * *